United States Patent
Schork et al.

(12) 
(10) Patent No.: US 6,297,188 B1
(45) Date of Patent: Oct. 2, 2001

(54) MAGNESIUM ETHOXIDE HAVING A HIGH COARSE PARTICLE CONTENT, PROCESS FOR ITS PREPARATION AND ITS USE

(75) Inventors: Reinhold Schork, Rheinfelden; Burkhard Standke, Loerrach; Hartwig Rauleder, Rheinfelden; Albert-Johannes Frings, Rheinfelden; Michael Horn, Rheinfelden; Peter Jenkner, Rheinfelden; Jaroslaw Monkiewicz, Rheinfelden, all of (DE)

(73) Assignee: Degussa-Huels Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/427,926

(22) Filed: Oct. 27, 1999

(30) Foreign Application Priority Data

Oct. 27, 1998 (DE) .............................. 198 49 353

(51) Int. Cl.⁷ .......................... B01J 31/00; B01J 27/138
(52) U.S. Cl. ..................... 502/171; 568/851; 502/169; 502/172; 502/226
(58) Field of Search ...................... 502/169, 171, 502/172, 226; 568/851

(56) References Cited

U.S. PATENT DOCUMENTS

| | | |
|---|---|---|
| 3,657,361 | 4/1972 | Lenz et al. . |
| 4,876,230 * | 10/1989 | Job ........................................ 502/171 |
| 5,210,334 | 5/1993 | Standke et al. . |
| 5,227,542 | 7/1993 | Horns et al. . |
| 5,456,801 | 10/1995 | Rauleder et al. . |
| 5,468,705 | 11/1995 | Rauleder et al. . |
| 5,468,706 | 11/1995 | Rauleder et al. . |

FOREIGN PATENT DOCUMENTS

| | | | |
|---|---|---|---|
| 34 12 337 | 10/1985 | (DE) . | |
| 0 091 425 * | 10/1983 | (EP) .................................... | 568/851 |
| 2 210 596 | 7/1974 | (FR) . | |
| 58-41832 * | 3/1983 | (JP) .................................... | 568/851 |
| 3-74341 * | 3/1991 | (JP) .................................... | 568/851 |

OTHER PUBLICATIONS

Patent Abstracts of Japan, vol. 011, No. 115 (C–415), Apr. 10, 1987, JP 61 260086, Nov. 18, 1986.

Derwent Publications, AN 1996–205468, JP 08 073388, Mar. 19, 1996.

* cited by examiner

*Primary Examiner*—Elizabeth D. Wood
*Assistant Examiner*—J. Pasterczyk
(74) *Attorney, Agent, or Firm*—Oblon, Spivak, McClelland, Maier & Neustadt, P.C.

(57) ABSTRACT

Particulate magnesium ethoxide having a high coarse particle content can be obtained in a simple and economical manner by the present invention, which provides a process for preparing particulate magnesium ethoxide having a coarse grain content, and includes reacting metallic, optionally activated, magnesium with liquid ethanol under pressure at a temperature above 78° C. The present invention also relates to particulate magnesium ethoxide having a coarse grain content, which contains:

<40% by weight of a screening fraction $\leq 500$ μm and
$\geq 60\%$ by weight of a screening fraction >500 μm.

14 Claims, No Drawings

MAGNESIUM ETHOXIDE HAVING A HIGH COARSE PARTICLE CONTENT, PROCESS FOR ITS PREPARATION AND ITS USE

BACKGROUND OF THE INVENTION

1. Field of the Invention

The present invention relates to a particulate magnesium ethoxide having a coarse particle content, to a process for its preparation and to its use.

2. Discussion of the Background

Processes for preparing magnesium ethoxide have been known for a considerable time. One industrial preparation route is the direct synthesis from metallic magnesium and ethanol. This is described, for example, by H. D. Lutz in Zeitschrift for anorganische und allgemeine Chemie, Volume 356, 1968, pages 132 ff. A catalyst is typically required to start the reaction and, generally, iodine is used as the catalyst. Magnesium ethoxide prepared in this manner disadvantageously includes traces of the starter catalyst, which can have adverse consequences, for example, when the resultant magnesium ethoxide is used as a catalyst precursor for Ziegler catalysts or for book preservation. If catalysts are not used, however, the reaction between ethanol and magnesium is not reliably initiated; and uncontrollable initiation behavior inheres great risk in industrial processes.

In the known processes for preparing magnesium ethoxide, long reaction times are also economically prohibitive. For example, for the complete reaction of ethanol magnesium to occur, reaction times of more than 24 hours are required. If the reaction is terminated prematurely, incompletely reacted metallic magnesium remains in the mixture together with magnesium ethoxide; and separation cannot be reasonably zarried out with standard equipment. In addition, the metallic magnesium impairs the properties of magnesium ethoxide.

Finally, the synthesis of magnesium ethoxide by known processes always produces magnesium ethoxide having considerable amounts of undesirable, undersized grains. This fine grain or dust content likewise impairs the properties of ihe product. This product content can be removed only with a great deal of expense during the preparation of magnesium ethoxide, for example by sieving or classifying, and discarding. It is desirable, therefore, to provide a process which enables the production of magnesium ethoxide in a particularly economical manner.

SUMMARY OF THE INVENTION

Accordingly, one object of the present invention is to provide a magnesium ethoxide having a high coarse particle content in a simple and economic manner.

Another object of the present invention is to provide a process for making a magnesium ethoxide having a high coarse particle content that is simple and economically feasible.

Surprisingly, it has now been found that particulate magnesium ethoxide having a high coarse particle content can be obtained in a simple and economical manner by the present invention, the first embodiment of which relates to EL process for preparing particulate magnesium ethoxide having a coarse grain content, includinig reacting metallic, optionally activated, magnesium with liquid ethanol under pressure at a temperature above 78° C.

Another embodiment of the present invention relates; to a particulate magnesium ethoxide having a coarse grain content, which contains:

<40% by weight of a screening fraction $\leq 500$ μm and
$\geq 60\%$ by weight of a screening fraction >500 μm.

The process according to the present invention can be reliably started in a simple and economical manner and without a catalyst contaminating the product. In addition, the present process can completely avoid the unwanted residue of incompletely reacted metallic magnesium. The reaction times of the present process are generally markedly less than 24 hours, which inheres a particularly economical mode of operation. Furthermore, a product having a comparatively low content of unwanted undersize grain or dust content is obtained.

BRIEF DESCRIPTION OF THE PREFERRED EMBODIMENTS

A more complete appreciation of the invention and many of the attendant advantages thereof will be readily obtained as the same becomes better understood by reference to the following detailed description of the preferred embodiments.

Preferably, in the process according to the present invention, metallic, optionally activated, magnesium is brought into contact with anhydrous ethanol in the liquid phase under pressure at a temperature above the boiling temperature of ethanol at atmospheric pressure (78° C.), the mixture is reacted to completion and the product is isolated.

Preferably, in the reaction according to the invention, liquid ethanol and solid metallic magnesium are brought into contact and heated under pressure to a temperature above 78° C. in such a manner that liquid ethanol is available as a reaction partner, and the hydrogen that is formed is ejected from the reaction space.

Preferably, to carry out the reaction according to the invention, dried ethanol is used in excess, so that ethanol can simultaneously serve as solvent. The magnesium ethoxide arising in the reaction according to the invention is then preferably isolated by filtration or by concentrating the product mixture at a temperature in the range from 0° to 180° C. under reduced pressure. More preferably, the isolation temperature ranges from 5° to 150° C., even more particularly preferably 10° to 125° C., and most preferably 15° to 100° C. Prior to product isolation, the resulting product mixture can be preferably cooled to a temperature of 20° to 78° C. More preferably, the cooling temperature ranges from 25° to 75° C., even more particularly preferably 30° to 70° C., and most preferably 35° to 65° C.

Preferably, both the reaction according to the invention and the isolation of the magnesium ethoxide according to the invention are carried out under a protective gas. A $CO_2$-free protective gas which has been dried in a manner known per se is preferably used, for example nitrogen or argon. Nitrogen, dried and $CO_2$-free, is most preferred.

Most preferably, the present invention relates to a process for preparing particulate magnesium ethoxide having a coarse grain content, wherein metallic, optionally activated, magnesium is reacted with ethanol in the liquid phase and subsequently the magnesium ethoxide is isolated, which includes carrying out the reactio:, under pressure at a temperature above 78° C.

Preferably, in the process according to the invention, the reaction temperature is set to a value of from >78 to 200° C., particularly preferably from 80 to 130° C., very particularly preferably from 100 to 130° C., and the pressure in the reaction space is set to a value above 1 bar absolute, particularly preferably to a value of from 2 to 6 bar absolute.

The metallic magnesium used in the process according to the invention preferably has a particle size of from 20 to 5000 μm. Preferably, it is used as pure magnesium metal. However, before the reaction, it can also be activated, for example by etching.

To start the reaction, a catalyst may be preferably added to the reaction mixture. The catalyst is preferably made of an inorganic or organic halogen compound, preferably a mercury halide, an inorganic or organic acid, such as HCl or acetic acid, or an alkyl orthoformate, such as tetraethyl orthoformate (TEOF).

Preferably, in the process according to the invention, the reaction is started by raising the temperature briefly to above 78° C., and more preferably >90° C. Preferably, in the further course of the reaction, the peak of hydrogen development proceeds at a temperature below 90° C.; the resulting hydrogen is conducted away from the reaction space; and the remaining reaction proceeds at a temperature above 90° C., likewise with ejection of the hydrogen formed. Preferably, the reaction has generally proceeded quantitatively after 16 hours, so that in an advantageous manner, virtually no magnesium metal residues remain in the product mixture. The product is generally isolated from the product mixture in the manner described above.

Particulate magnesium ethoxide prepared according to the invention advantageously has a high content of coarse grains. The grain content is generally determined under dry protective gas by screening analysis according to the usual methods.

The present invention therefore also relates to a particulate magnesium ethoxide having a coarse grain content by weight, containing <40% of a screening fraction ≦500 μm (mesh width) and ≧60% by weight of a screening fraction >500 μm.

Preferably, magnesium ethoxide according to the invention contains ≧80% by weight of a screening fraction >500 μm (mesh width).

Most preferably in the magnesium ethoxide according to the invention, the content of a screening fraction >800 μm (mesh width) is more than 40% by weight, based on the total amount.

In addition, magnesium ethoxide according to the invention preferably contains less than 10% by weight, particularly preferably from 0.01 to 5% by weight, of a screening fraction <315 μm (mesh width). That is to say that particulate magnesium ethoxide according to the invention has a high content of coarse grain, which is very desirable and particularly economical; and, in a particularly surprising and advantageous manner, only a comparatively low content of undersize grain, and the content of fine dust virtually (and desirably) approaching zero.

Preferably, the process according to the invention is carried out as follows: nitrogen, anhydrous ethanol and particulate metallic magnesium are introduced under a dry protective gas atmosphere into a heatable stainless steel pressure reactor equipped with an adjustable overpressure valve, and the mixture is heated to a temperature above 78° C. A pressure above ambient pressure can develop in the sealed reactor owing to the vapor pressure of the ethanol used and the development of hydrogen according to reaction 1.

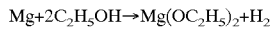   Reaction 1

If this exceeds the limit set at the overpressure valve, the valve can open and hydrogen and ethanol vapor may escape. The expanded gas mixture is generally passed through a cooler, with ethanol condensing, while hydrogen is conducted away in a gaseous state. The condensed ethanol can be recirculated to the reactor via a metering pump which can overcome the overpressure prevailing in the reactor. This reaction procedure has the particular advantage that it is not necessary to use a condensation system suitable for overpressure. If an overpressure-safe condensation system is available, the overpressure control valve can likewise be mounted at the top of the condensation system in such a manner that the expanded gas downstream of the pressure control valve principally contains hydrogen. The condensation system reflux, ethanol, is generally recirculated to the reactor, so that recycling of ethanol with overcoming of pressure can be avoided.

Preferably, the reaction can also be started at atmospheric pressure, e.g. with the use of catalysts known from the literature, such as halogens, halogen compounds, acids, mercurn compounds or alkyl orthoformates, and can then be continued with an increase in pressure. This generally has the advantage that pressure peaks caused by the initially very vigorous reaction at elevated temperature (>78° C.) can be made less xtreme. An unmanageable pressure increase in the reactor represents a considerable hazard potential.

A further preferred method for the reaction procedure includes beginning the reaction in the absence of catalyst at atmospheric pressure and the boiling temperature of ethanol (78° C.) and increasing the pressure and temperature in the plant as the reaction progresses. Pressure peaks can likewise be avoided in this manner. If problems with respect to initiating the reaction should exist, the reaction can be started by a brief increase in the temperature and pressure. Immediately after the start of the reaction, uncontrolled hydrogen development can be checked by decreasing the pressure and temperature in the reactor by expansion via the pressure control valve.

The product is preferably isolated in the process according to the invention in the above-mentioned manner.

In addition, the process according to the invention has the advantage that when particulate magnesium having a mean particle size >200 μm, preferably ≧800 μm, is used, the reaction time is less than 24 hours, no metallic magnesium remains in the product and significantly fewer undersize grain are produced than when the product is prepared at atmospheric pressure by conventional processes.

Preferably, the particulate magnesium ethoxide according to the invention having a coarse grain content, on account of its advantageous properties, is particularly suitable as a precursor for Ziegler-Natta catalysts, as a precursor for ceramics and a precursor for book preservation media.

EXAMPLES

Having generally described this invention, a further understanding can be obtained by reference to certain specific examples, which are provided herein for purposes of illustration only and are not intended to be limiting unless otherwise specified.

Reaction Apparatus:

1-1 stainless-steel autoclave with close-clearance agitator. pressure measuring device (aneroid manometer), temperature measuring device (Pt 100 sensor, temperature control via thermostat, liquid metering pump (diaphragm pump Prominent Gamma/4-/, adjustable overpressure valve, condensation system (intensive glass cooler), gas meter (drum gas meter TG3, Ritter) and protective gas blanketing (nitrogen).

Drying Apparatus:

Protective gas (nitrogen)-blanketed laboratory rotary evaporator (2-1 glass evaporator flask) with vacuum facility.

Reaction Procedure:

24.3 g of particulate metallic magnesium (d50>800 μm, purity: >99%) are introduced together with 356 g of ethanol under a protective gas curtain into a stainless-steel autoclave. After sealing the apparatus, the overpressure valve is set to the desired internal reactor pressure and the mixture is brought to reaction temperature. On reaching the preset temperature and the preset pressure, hydrogen and ethanol vapor escape via the pressure control valve into the condensation system. Ethanol condensed out is pumped back into the reactor via the diaphragm metering pump at the rate at which condensate is formed in the cooler. The resulting hydrogen is removed from the reaction apparatus via the drum gas meter. The volumetric flow rate of hydrogen is measured. If hydrogen development can no longer be observed, the reaction is terminated by depressurizing and cooling the reactor. The suspension (magnesium ethoxide in ethanol) is transferred to the 2-1 flask of the rotary evaporator and dried there in the course of 2.5 hours at 100° C. and under reduced pressure (to 1 mbar). The product is then subjected to a particle size analysis (screening analysis). In addition, the content of incompletely reacted metallic magnesium is determined indirectly from the amount of hydrogen formed on adding aqueous hydrochloric acid to the product.

1. (NP6994) Preparation of magnesium ethoxide from ethanol and magnesium at 110° C. and a pressure of 3 bar The procedure as described under "reaction procedure" is followed. The temperature of the heating medium (silicone oil) of the thermostat is 170° C. At a pressure of 3 bar in the reactor, the temperature in the reactor is 110° C. Approximately 5 minutes after reaching the reaction temperature, the maximum hydrogen development of approximately 30 l/h is measured. The reaction is complete after approximately 6 hours; no more hydrogen development occurs. The product is dried and analyzed as described above.

| Screening Analysis | |
|---|---|
| >800 μm | 55.7% by weight |
| 500–800 μm | 36.4% by weight |
| 315–500 μm | 7.1% by weight |
| 200–315 μm | 0.6% by weight |
| 100–200 μm | 0% by weight |
| <100 μm | 0.1% by weight |
| Metallic Magnesium | <0.02% by weight |

2. (NP6694) Preparation of magnesium ethoxide from ethanol and magnesium at 120° C. and a pressure of 4 bar The procedure as described under "reaction procedure" is followed. The temperature of the heating medium (silicone oil) of the thermostat is 170° C. At a pressure of 4 bar in the reactor, the temperature in the reactor is 120° C. Approximately 5 minutes after reaching the reaction temperature, the maximum hydrogen development of approximately 35 l/h is measured. The reaction is complete after approximately 3.5 hours; no more hydrogen development occurs. The product is dried and analyzed as described above.

| Screening Analysis | |
|---|---|
| >800 μm | 46.2% by weight |
| 500–800 μm | 36.4% by weight |
| 315–500 μm | 13.1% by weight |
| 200–315 μm | 3.3% by weight |
| 100–200 μm | 0.8% by weight |
| <100 μm | 0.1% by weight |
| Metallic Magnesium | <0.02% by weight |

3. Preparation of magnesium ethoxide from ethanol and magnesium at 78° C. and atmospheric pressure (1 bar, comparative example, NP6894)

The procedure as described under "reaction procedure" is followed, but with the difference that the magnesium turnings used are washed with 0.1 N aqueous HCl to remove the oxide layer and dried under protective gas at 100° C. to increase the reactivity; the reaction is not reliably initiated without this step. The temperature of the heating medium (silicone oil) of the thermostat is 120° C. At a pressure of 1 bar in the reactor (atmospheric pressure), the temperature in the reactor is 78° C. Approximately 5 minutes after reaching the reaction temperature, the maximum hydrogen development of approximately 6 l/h is measured. After approximately 7 hours, a sample is taken from the reactor. The reaction product still contains considerable amounts of incompletely reacted magnesium which is visible to the eye. Hydrogen development is not complete until after a reaction time of more than 24 hours, and the reactor is cooled. The product is dried and analyzed as described above.

| Screening Analysis | |
|---|---|
| >800 μm | 5.9% by weight |
| 500–800 μm | 39.5% by weight |
| 315–500 μm | 42.9% by weight |
| 200–315 μm | 8.6% by weight |
| 100–200 μm | 2.6% by weight |
| <100 μm | 0.5% by weight |
| Metallic Magnesium | <0.02% by weight |

The particle size distribution shows a marked increase of unwanted undersized grain (content of particles <315 μm is >11%).

Obviously, numerous modifications and variations of the present invention are possible in light of the above teachings. It is therefore to be understood that within the scope of the appended claims, the invention may be practiced otherwise than as specifically described herein.

This application is based on German patent application DE 19849353.3, filed Oct. 27, 1998, the entire contents of which are hereby incorporated by reference.

What is claimed is:

1. A particulate magnesium ethoxide having a coarse grain content comprising:

<40% by weight of a screening fraction ≦500 μm and

≧60% by weight of a screening fraction >500 μm.

2. The particulate magnesium ethoxide as claimed in claim 1, comprising <10% by weight of a screening fraction <315 μm.

3. The particulate magnesium ethoxide as claimed in claim 1, comprising from 0.01 to 5% by weight of a screening fraction <315 μm.

4. The particulate magnesium ethoxide as claimed in claim 1, comprising ≧80% by weight of a screening fraction >500 μm.

5. The particulate magnesium ethoxide as claimed in claim 1, comprising >40% by weight of a screening fraction >800 μm.

6. The particulate magnesium ethoxide as claimed in claim 1, which is produced by a process comprising reacting metallic, optionally activated, magnesium with liquid ethanol under pressure at a temperature above 78° C.

7. A process for preparing particulate magnesium ethoxide comprising:
   <40% by weight of a screening fraction ≦500 μm and
   ≧60% by weight of a screening fraction >500 μm,
   said process comprising reacting metallic, optionally activated, magnesium with liquid ethanol under pressure of above 1 bar absolute at a temperature of above 78° C.

8. The process as claimed in claim 7, wherein the liquid ethanol and metallic magnesium are contacted with one another in a reaction space, wherein hydrogen is formed and removed from the reaction space.

9. The process as claimed in claim 7, wherein the reaction temperature is between 78 and 200° C., exclusive of 78° C.

10. The process as claimed in claim 8, wherein hydrogen is formed and wherein the peak of hydrogen formation proceeds at a temperature below 90° C., and wherein the hydrogen is removed from the reaction space.

11. The process as claimed in claim 7, wherein the metallic magnesium has a particle size of 20 to 5000 μm.

12. The process as claimed in claim 7, further comprising raising the temperature to above 90° C. at the start of the reaction.

13. The process as claimed in claim 12, further comprising continuing the reaction at a temperature above 90° C.

14. A precursor for a Ziegler-Natta catalyst, comprising the magnesium ethoxide as claimed in claim 1.

* * * * *